though highly effective insecticides. When applied to insects, they cannot be detected 24 hours later, because of the ease with which they are metabolized, principally to the p-p'dimethoxybenzhydrol, which has a low order of insect toxicity. Thus, the p-methylthio compound has been shown to disappear rapidly from mouse liver homogenates containing nicotinamide adenine dinucleotide phosphate ("NADPH") cofactor, substantially as described in Science, Vol. 164, p. 856 (1969).

United States Patent
Metcalf et al.

[11] 3,932,527

[45] Jan. 13, 1976

[54] PREPARATION OF P-P-DISUBSTITUTED DIARYL TRICHLOROETHANES

[75] Inventors: Robert L. Metcalf; Asha Hirwe, both of Urbana, Ill.

[73] Assignee: University of Illinois Foundation, Urbana, Ill.

[22] Filed: Nov. 19, 1973

[21] Appl. No.: 417,420

[52] U.S. Cl........ 260/609 F; 260/609 E; 260/612 R; 260/613 R; 260/649 DD; 424/337; 424/354; 424/341
[51] Int. Cl.².................................. C07C 149/32
[58] Field of Search.............. 424/337, 341, 354; 260/613 R, 612 R, 609 F, 649 DD, 609 E

[56] References Cited
UNITED STATES PATENTS

| | | | |
|---|---|---|---|
| 3,548,009 | 12/1970 | Priddy et al..................... | 260/613 R |
| 3,642,910 | 2/1972 | Nolan............................. | 260/612 R |
| 3,657,357 | 4/1972 | Nolan ............................ | 424/341 |
| 3,787,505 | 1/1974 | Metcalf........................... | 260/612 R |

OTHER PUBLICATIONS

Chemical Abstracts, Vol. 75 (1971), p. 97552f.

*Primary Examiner*—V. D. Turner
*Attorney, Agent, or Firm*—Merriam, Marshall, Shapiro & Klose

[57] ABSTRACT

Preparation of insecticidal, biodegradable compositions comprising mixtures of p-p'disubstituted diaryl trichloroethanes. Chloral, and appropriate substitutal benzenes are condensed, in a single step, at low temperature, e.g., −30°C., using a condensing agent preferably consisting of a mixture of sulfuric acid and acetic acid.

5 Claims, No Drawings

PREPARATION OF P-P-DISUBSTITUTED DIARYL TRICHLOROETHANES

The present invention relates to biodegradable p-p' disubstituted diaryl trichloroethanes. In general, it concerns the preparation of mixtures of p-p' disubstituted diaryl trichloroethanes. More particularly, it involves a single-step synthesis in which the reactants are brought together substantially all at once in a manner which yields relatively inexpensive mixtures of p-p' asymmetrical disubstituted diaryl trichloroethanes having utility, for example, as biodegradable insecticides.

In commonly assigned copending patent application U.S. Ser. No. 147,247, filed May 26, 1971, now U.S. Pat. No. 3,787,505, we disclosed that certain asymmetrical disubstituted diaryl trichloroethanes are insecticidal, yet biodegradable, compositions which exhibit low toxicity to mammals. Such compositions, therefore, possess properties which overcome the major environmental pollutant problems associated with the use of DDT (1,1,1-trichloro-2,2-bis [p-chlorophenyl] ethane). However, the procedures heretofore used to prepare the compositions disclosed in said application have not yet resulted in the practical, economic commercial production of such compositions. Briefly, such procedures involved a "dropwise" addition of reactants to synthesize a reaction mixture which thereafter was processed, e.g., by steam distillation, to isolate the desired p-p' disubstituted diaryl trichloroethane. Thus, there arose a need for a practical, less expensive process for the preparation of p-p' disubstituted diaryl trichloroethanes.

Briefly, the present invention provides for the preparation of relatively inexpensive mixture of p-p' asymmetrical disubstituted diaryl trichloroethanes.

We have found that by the procedures of the present invention we can synthesize reaction mixtures in a single step and that the resulting mixtures need not be subjected to time consuming and hence costly isolation steps in order to obtain biodegradable p-p' disubstituted diaryl trichloroethanes.

In the synthesis step of the present invention, chloral and the desired substituted benzene compound(s) are contacted together in a manner hereinafter described more fully. During the synthesis, chloral and the substituted benzene compound(s) condense in the presence of an acidic condensing agent to yield a mixture of p-p' disubstituted diaryl trichloroethanes. The synthesis step is carried out at low temperature, i.e., below about 20°C. and preferably at about −30°C.

One very important aspect of the single step synthesis of the present invention is that the reactants are contacted or brought together substantially all at once. By this we mean to distinguish the relatively time consuming prior art procedure of "dropwise" addition of reactants disclosed, for example, in the above identified application, Ser. No. 147,247. In the present invention, during the synthesis step, the reactants are added or incorporated substantially all at once, or all at one time. This may be done, for example, in a batch operation by placing the reactants together in the reaction vessel, without regard to the sequence of addition. Moreover, this may also be done, for example, in a continuous operation provided the desired proportion or mole ratio of reactants is controlled throughout the synthesis step.

The acidic condensing agent employed in the present invention is either a mixture of sulfuric acid and glacial acetic acid or anhydrous aluminum trichloride. We have found that the reaction is sensitive to the relative proportions of sulfuric acid and glacial acetic acid employed. A preferred acidic condensing agent comprises a mixture of sulfuric acid and glacial acetic acid in a volume ratio in the range of about 90:10 to about 60:40, most preferably about 50:50.

During the synthesis step, the temperature is controlled so as to maintain low temperature throughout the reaction. In order to prevent sulfonation of the reaction product, the temperature of the reaction mass should generally be kept below about 20°C. A preferred temperature is generally in the range of about 0°C. to about −30°C. During the synthesis step, the reaction mass is preferably stirred or agitated. Reaction time in the range of about 2 to about 5 hours has been found to be generally effective, with about 4 hours appearing to be an optimum reaction time. The synthesis step is terminated by contacting the reaction mass with ice which dilutes the acidic condensing agent and causes the mixture of p-p' disubstituted diaryl trichloroethanes to crystallize, since the mixture is substantially water insoluble.

Following termination of the synthesis step by the addition of ice to the reaction mass, the crystallized, generally water insoluble, mixture of p-p' disubstituted diaryl trichloroethanes is recovered by separating it from the rest of the reaction mass. This may be accomplished, for example, by a simple solvent extraction step, employing a suitable solvent, e.g., chloroform, ether, benzene, and the like.

While the mixture thus recovered can, of course, be further processed in order to obtain relatively pure compounds, one important aspect of the present invention, exemplified hereinafter, is the discovery that the mixtures of p-p'-disubstituted diaryl trichloroethane have practical utility without the costly necessity of isolating specific pure compounds.

As mentioned above, the reactants employed in the present invention are chloral and one or more substituted benzenes. The particular substituted benzene(s) employed will, of course, depend, in part, upon the specific properties desired in the mixture. Generally, where a biodegradable mixture is desired, the substituted benzene is chosen so as to provide one or more $-CH_3$, $-CH_3O$, and/or $SCH_3$ moities in the p-p' asymmetrical disubstituted diaryl trichloroethane containing mixture. However, other election donating groups can also be used in the process, such as: $-C_2H_5O$, $-C_3H_7O$, $-C_2H_5$, and/or $-Cl$.

The present invention will be further understood by reference to the following illustrative examples.

EXAMPLE I

The preparation of a mixture containing 2-(p-methoxyphenyl)-2-(p-tolyl)-1,1,1-trichloroethane was carried out as follows:

Anisole (2.84 gms., 0.017 mole), toluene (4.6gms., 0.05 mole), and chloral (7.35 gms., 0.05 mole) were added to a 60:40 (volume ratio) mixture of sulfuric acid and glacial acetic acid (25 ml) in an erlenmeyer flask cooled to −20°C. The resulting mixture was stirred for 4 hours during which time the temperature of the reaction mass was maintained at 0°. Thereafter the synthesis step was terminated by pouring the reaction mass onto ice. The cooled, diluted reaction mass was extracted with chloroform. Evaporation of the chloroform left a waxy solid material which when subjected to gas chromatography gave the following analysis:

acid and acetic acid, as shown in Table I. The toxicity of some of the mixtures resulting from various conditions of synthesis was tested by standard techniques well known in the art, the results of which are also shown in Table I.

TABLE I

Synthesis of mixtures containing:

[structure: $CH_3$—phenyl—CH(CCl$_3$)—phenyl—$OCH_3$]

| Reactants (moles) | | Condensing Agent (volume %) | | Composition of Resulting Mixture (yield %) | | | Toxicity* topical LD$_{50}$ Musca domestica |
|---|---|---|---|---|---|---|---|
| anisole | toluene | H$_2$SO$_4$ | HAc | CH$_3$—OCH$_3$ | CH$_3$O—OCH$_3$ | CH$_3$—CH$_3$ | Mg. per. $^\circ$ |
| 0.05 | 0.05 | 90 | 10 | 31 | 16 | 53 | — |
| 0.05 | 0.05 | 80 | 20 | 13 | 46 | 41 | — |
| 0.05 | 0.05 | 70 | 30 | 16 | 84 | — | — |
| 0.05 | 0.05 | 60 | 40 | 14 | 86 | — | — |
| 0.05 | 0.05 | 50 | 50 | 1 | 99 | — | — |
| 0.025 | 0.05 | 60 | 40 | 40 | 60 | — | 0.88 |
| 0.017 | 0.05 | 60 | 40 | 60 | 40 | — | 0.65 |
| 0.025 | 0.05 | 70 | 30 | 32 | 24 | 44 | — |
| 0.017 | 0.05 | 70 | 30 | 36 | 34 | 30 | — |
| 0.012 | 0.05 | 60 | 40 | 46 | 54 | — | 0.83 |
| 0.012 | 0.05 | 65 | 35 | 44 | 56 | — | 0.87 |

*The toxicity data was obtained by treating 2–4 day old female houseflies with standard w/v solutions applied to the pronotum. Three replicates of 20 flies each were run at 4 to 5 dosages and the LD$_{50}$ data obtained from log dosage vs. probit mortality plots. LD$_{50}$ value for a 1:1 mixture of 99% pure CH$_3$—OCH$_3$ and 99% pure CH$_3$O—OCH$_3$ is 0.62 Mg per $^\circ$. LD$_{50}$ for CH$_3$—OCH$_3$ is 0.47 Mg per $^\circ$.

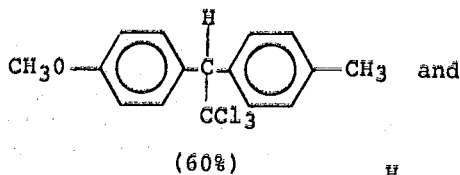

(60%)

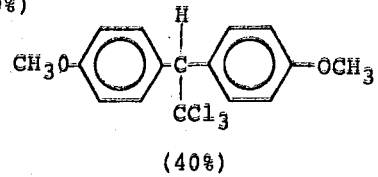

(40%)

The reaction exemplified above was found to be sensitive to the relative concentration of the substituted benzene reactants and to the proportionality of sulfuric

EXAMPLE II

A procedure identical to that employed in Example I was applied to the synthesis of a mixture containing 2-(p-ethoxyphenyl)-2-(p-tolyl)-1,1,1-trichloroethane. The optimum conditions for maximum yield of the desired product were found to be a 70:30 (volume ratio) mixture of sulfuric acid and glacial acetic acid about 0.025 moles of phenetol, 0.05 moles of toluene, and 0.05 moles of chloral. Table II shows the effects of variations in synthesis conditions upon the amounts of the various products formed.

TABLE II

Synthesis of mixtures containing:

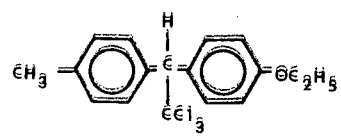

| Reactants (moles) | | Condensing Agent (volume %) | | Composition of Resulting Mixture (yield %) | | | Toxicity* topical LD$_{50}$ Musca domestica |
|---|---|---|---|---|---|---|---|
| phenetol | toluene | H$_2$SO$_4$ | HAc | CH$_3$—OC$_2$H$_5$ | C$_2$H$_5$O—OC$_2$H$_5$ | CH$_3$—CH$_3$ | Mg. Per+ |
| 0.05 | 0.05 | 60 | 40 | — | 99.5 | — | — |
| 0.017 | 0.05 | 60 | 40 | 45 | 55 | — | 0.55 |
| 0.025 | 0.05 | 60 | 40 | 21 | 79 | — | 0.48 |
| 0.017 | 0.05 | 70 | 30 | 51 | 49 | — | 0.47 |
| 0.025 | 0.05 | 70 | 30 | 59 | 7.5 | 33 | 0.87 |
| 0.017 | 0.05 | 50 | 50 | — | 100 | — | — |
| 0.0125 | 0.05 | 60 | 40 | 30 | 70 | — | 0.54 |

+LD$_{50}$ value for a 1:1 mixture of 99% pure CH$_3$—OC$_2$H$_5$ and 99% pure C$_2$H$_5$O—OC$_2$H$_5$ is 0.31 Mg per $^\circ$. LD$_{50}$ for CH$_3$—OC$_2$H$_5$ is 0.18 Mg per $^\circ$.

EXAMPLE III

Synthesis of mixtures containing 2-(p-methoxyphenyl)-2-(p-methylthiophenyl)-1,1,1-trichoroethane was prepared by the present invention as follows:

A mixture of anisole (10.8g., 0.1 mole), thioanisole (12 g., 0.1 mole), and chloral 14.7 g. (0.1 mole) was stirred into anhydrous $AlCl_3$ (14.7 g., 0.1 mole) in 100 ml chloroform. The reaction mixture was left overnight, poured onto ice and extracted with chloroform. The extract was dried with $CaCl_2$ and the chloroform removed to give an oil which crystallized from ethanol. Gas chromatography indicated the following composition:

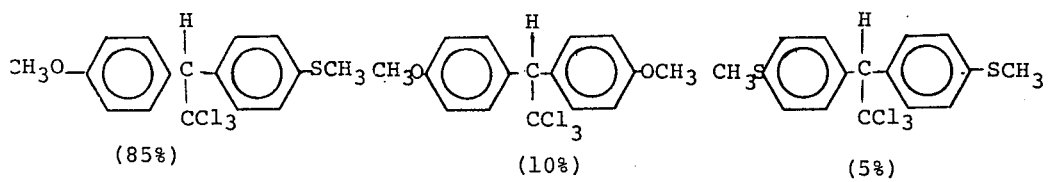

Compositions prepared by the present invention can be formulated into insecticidal formulations using techniques known to the art in the formulation of DDT insecticides. Thus, dust, water dispersion, emulsions and their solutions can be formulated, provided however that the carrier or solvent is compatible and inert in the sense that it does not react or interfere with the insecticidal and biodegradable characteristics of the mixtures of the p,p' disubstited diaryl trichloroethanes.

While the present invention has been described by reference to illustrative examples, various modifications will be apparent to those skilled in the art and any such modifications are intended to be within the spirit and scope of the invention as defined by the appended claims.

What is claimed is:

1. A process for preparing mixtures of asymmetrical p-p'-disubstituted diphenyl trichloroethanes which comprises reacting chloral and a substituted benzene, wherein the substituents are selected from the group consisting of $—CH_3$, $—CH_3O$, $—SCH_3$, $—C_2H_5O$, $—C_3H_7O$, $—C_2H_5$ and $—CL$, together substantially all at once in the presence of an acidic condensing agent selected from the group consisting of (1) a mixture of sulfuric acid-glacial acetic acid and (2) anhydrous aluminum trichloride and at a low temperature in the range of about 0°C to about −30°C, the amount of chloral and substituted benzene being sufficient to form the said trichloroethanes.

2. A process as defined in claim 1 wherein said acidic condensing agent comprises a mixture of sulfuric acid and glacial acetic acid.

3. A process as defined in claim 1 wherein said acidic condensing agent comprises anhydrous aluminum trichloride.

4. A process as defined by claim 1 wherein the reaction product is subsequently solvent extracted to yield a mixture of p-p'-disubstituted diphenyl trichloroethanes.

5. A process for preparing mixtures of asymmetrical p-p'-disubstituted diphenyl trichloroethanes which comprises reacting chloral and a substituted benzene, wherein the substituents are selected from the group consisting of $—CH_3$, $—CH_3O$, $—SCH_3$, $—C_2H_5O$, $—C_3H_7O$, $—C_2H_5$ and $—Cl$, together substantially all at once in the presence of an acidic condensing agent comprising a mixture of sulfuric acid and glacial acetic acid in a volume ratio of about 50:50 and at a low temperature in the range of about 0°C. to about −30°C.

* * * * *